(12) United States Patent
Clark et al.

(10) Patent No.: US 7,671,978 B2
(45) Date of Patent: Mar. 2, 2010

(54) SCATTEROMETER-INTERFEROMETER AND METHOD FOR DETECTING AND DISTINGUISHING CHARACTERISTICS OF SURFACE ARTIFACTS

(75) Inventors: Bryan Clark, Mountain View, CA (US); Andrei Brunfeld, Cupertino, CA (US); Gregory Toker, Jerusalem (IL)

(73) Assignee: Xyratex Technology Limited, Havant, Hampshire (GB)

( * ) Notice: Subject to any disclaimer, the term of this patent is extended or adjusted under 35 U.S.C. 154(b) by 358 days.

(21) Appl. No.: 11/739,210

(22) Filed: Apr. 24, 2007

(65) Prior Publication Data

US 2008/0266547 A1 Oct. 30, 2008

(51) Int. Cl.
*G01N 21/00* (2006.01)
*G01B 11/02* (2006.01)

(52) U.S. Cl. .............. 356/73; 356/237.1; 356/511

(58) Field of Classification Search .............. 356/73
See application file for complete search history.

(56) References Cited

U.S. PATENT DOCUMENTS

| 5,235,192 | A |   | 8/1993 | Chase et al. |
| 5,790,251 | A |   | 8/1998 | Hagiwara |
| 5,923,423 | A | * | 7/1999 | Sawatari et al. ........ 356/484 |
| 6,201,601 | B1 |   | 3/2001 | Vaez-Iravani et al. |
| 6,522,471 | B2 |   | 2/2003 | Clark |
| 6,653,649 | B2 |   | 11/2003 | Clark |
| 6,700,840 | B2 |   | 3/2004 | Clark |
| 6,714,295 | B2 |   | 3/2004 | Clark |
| 6,717,707 | B2 |   | 4/2004 | Clark |
| 6,757,056 | B1 |   | 6/2004 | Meeks et al. |
| 6,774,987 | B2 |   | 8/2004 | Komatsu et al. |
| 6,778,307 | B2 |   | 8/2004 | Clark |
| 6,829,559 | B2 |   | 12/2004 | Bultmann et al. |
| 6,879,390 | B1 |   | 4/2005 | Kvamme et al. |
| 6,879,421 | B2 |   | 4/2005 | Clark et al. |
| 6,891,610 | B2 | * | 5/2005 | Nikoonahad et al. ...... 356/237.2 |
| 6,898,037 | B2 |   | 5/2005 | Leigh et al. |
| 6,917,419 | B2 |   | 7/2005 | Fielden et al. |
| 6,927,864 | B2 |   | 8/2005 | Clark |
| 6,934,032 | B1 |   | 8/2005 | Subramanian et al. |
| 6,937,333 | B2 |   | 8/2005 | Horie et al. |
| 6,986,280 | B2 |   | 1/2006 | Muckenhirm |
| 6,999,183 | B2 |   | 2/2006 | Nielsen et al. |
| 7,022,978 | B2 |   | 4/2006 | Clark et al. |
| 7,102,740 | B2 |   | 9/2006 | Clark et al. |

(Continued)

OTHER PUBLICATIONS

U.S. Appl. No. 11/143,018, filed Jun. 1, 2005, Brunfeld, et al.

(Continued)

*Primary Examiner*—Michael A Lyons
(74) *Attorney, Agent, or Firm*—Mitch Harris, Atty at Law, LLC; Andrew M. Harris

(57) ABSTRACT

A scatterometer-interferometer and method for detecting and distinguishing characteristics of surface artifacts provides improved artifact detection and increased scanning speed in interferometric measurement systems. A scatterometer and interferometer are combined in a single measurement head and may have overlapping, concentric or separate measurement spots. Interferometric sampling of a surface under measurement may be initiated in response to detection of a surface artifact by the scatterometer, so that continuous scanning of the surface under measurement can be performed until further information about the size and/or height of the artifact is needed.

36 Claims, 12 Drawing Sheets

U.S. PATENT DOCUMENTS 7,193,725 B2 3/2007 Brunfeld et al.
2008/0180656 A1* 7/2008 Meeks et al. .................. 356/73

OTHER PUBLICATIONS

U.S. Appl. No. 11/149,094, filed Jun. 8, 2005, Toker, et al.
U.S. Appl. No. 11/167,807, filed Jun. 27, 2005, Brunfeld, et al.
U.S. Appl. No. 11/156,309, filed Jun. 17, 2005, Brunfeld, et al.
U.S. Appl. No. 11/169,517, filed Jun. 29, 2005, Brunfeld, et al.
Riesz "Makyoh Topography for the Study of Large-Area Defects in the Surface of Semiconductors", Hungarian Academy of Sciences, Budapest, Oct. 1998.

* cited by examiner

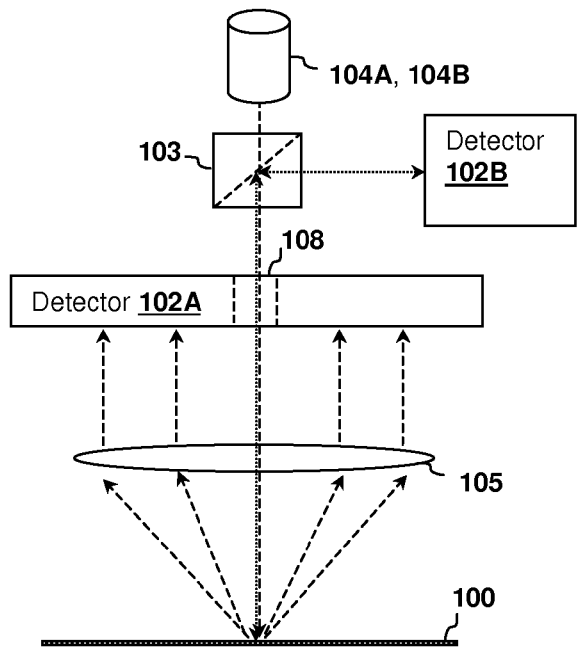
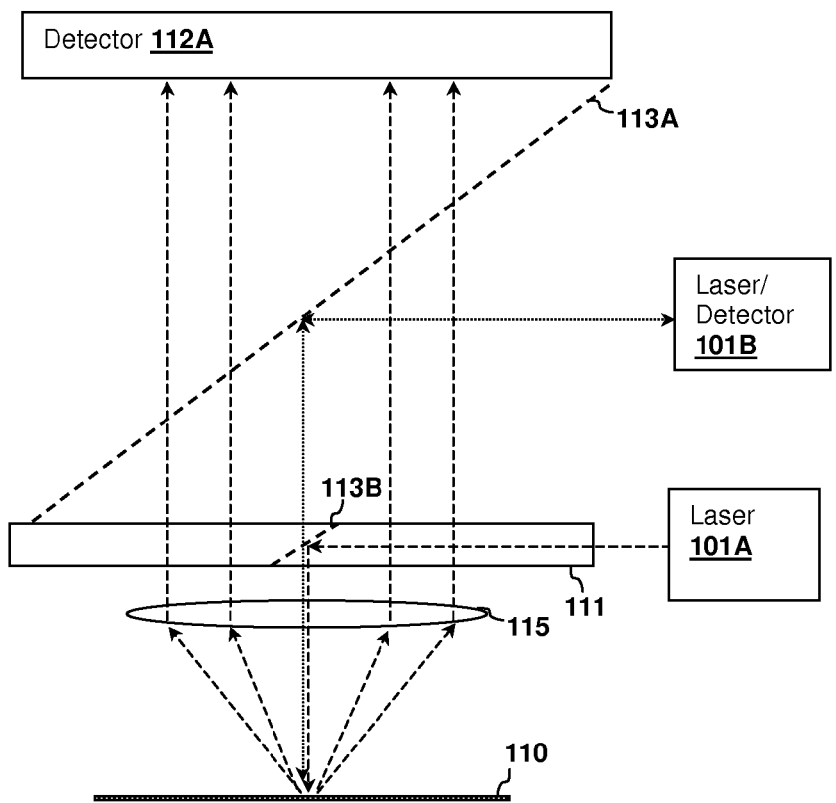
Fig. 11
Fig. 12

SCATTEROMETER-INTERFEROMETER AND METHOD FOR DETECTING AND DISTINGUISHING CHARACTERISTICS OF SURFACE ARTIFACTS

BACKGROUND OF THE INVENTION

1. Field of the Invention

This invention relates to optical systems, and more specifically, to a scatterometer-interferometer optical inspection head and system and method for measuring surface topology and for detecting and distinguishing characteristics of surface defects.

2. Background of the Invention

Optical surface inspection systems are in common use in industry to determine whether surface features are present on an article as desired, and further whether undesirable defects or contaminants are also present.

Scatterometers are well-known and commonly used in surface inspection systems to determine whether defects are present. Since scatterometers typically operate in dark-field mode, they are very sensitive to the sharp increase in intensity due to the presence of a defect, feature or contaminant on a surface. Scatterometers are also tolerant of variation in source intensity and to some degree, source alignment. However, scatterometers do not typically yield much information about a surface artifact other than its location and presence. Hence, scatterometers are typically not used when information about the size or nature of surface artifacts must be determined. Due to their dark-field detection, scatterometers can typically employ very sensitive and fast detectors such as photo-multipliers and can use very large "spot" sizes with high-intensity source illumination in order to detect small defects very quickly. Scatterometers are typically used in continuous scanning mode with a threshold on the detected reflection value(s) indicating only the presence of a defect within the spot.

Various differential methods have been used to single out artifacts on a surface, such as optical lever methods that measure local surface inclination, phase-contrast or differential interference contrast (DIC) microscopy. However, the differential methods mentioned above are not sensitive to defects that are too smooth to produce an appreciable difference. In addition, the above-described systems give only a relative indication that must be mathematically integrated in order to produce a full surface profile, a procedure that is mathematically error-prone.

Height measuring interferometry is the method of choice for characterization of surface topography including measurement of gross surface features such as inclination and curvature, as well as measuring individual surface artifacts. Of particular usefulness are interferometric methods that provide local height measurement using a single spot, as a direct measurement of an artifact can be made and such systems are amenable to scanning large surfaces. Such systems not only can measure topographic features or defects that only slightly scatter incident light, but can also distinguish height from depth (bump vs. pit defects), as well as providing actual height or depth magnitudes along with the lateral size of the features. For artifacts smaller than the spot size, although the interferometric signal combines both the height and size information so that the reported height/depth is typically smaller than the actual vertical dimension, true height and size information can be recovered by oversampling and deconvolution techniques well known in art.

Single-spot interferometers commonly used for height measurement include Michelson, fringe-counting, phase-shifting, and Doppler types. The advantage of the height measuring single-spot interferometers over other systems is that direct sampling of height is provided. Two-spot (differential) interferometers measure the height difference between neighboring spots, which will always include the local inclination angle in the direction of offset between the spots. In particular, surface topography is given directly in single-spot techniques whereas in differential techniques, the topography must be reconstructed by integration.

Recently, resonator-enhanced optical measurement systems have been introduced as disclosed in U.S. Pat. Nos. 6,714,295 and 6,927,864 and 7,022,978, the disclosures of which are incorporated herein by reference. The incorporation of a resonator in the inspection system greatly increases the sensitivity and/or resolution of the inspection system, so that smaller features and defects can be detected and information gathered about their size, height and properties. Resonator-enhanced interferometric systems have an even smaller spot size and therefore require even more sampling, and hence more computation, to produce accurate defect detection.

There are several drawbacks to interferometric height measurement for defect detection. Interferometric measurement is intrinsically a discrete (sampled) measurement rather than being continuous and defects that are small or have shallow profiles produce small signals close to the detection threshold may be missed. Also, most interferometers are inherently bright-field measurement systems, and are therefore sensitive to variations in source intensity and variations in surface reflectivity, which also may lead to missed defects and/or false triggers.

Therefore, it would be desirable to supplement an interferometric height measurement system that provides detailed information about the size and/or properties of a surface artifact with fast and sensitive artifact detection. It would further be desirable to provide such surface artifact detection in a resonator-enhanced interferometric measurement system such as the Fabry-Perot resonator-enhanced systems disclosed in the above-incorporated U.S. Patents.

SUMMARY OF THE INVENTION

The foregoing objectives are achieved in an optical system and method for optical measurement. The measurement system includes a height-measuring interferometer for measuring light reflected from a single interferometric spot on a surface under measurement, a scatterometer for measuring light scattered from a scatterometric spot on the surface under measurement, and a signal processor coupled to detectors of the interferometer and scatterometer for commencing interferometric measurement in response to detecting a surface artifact on the surface under measurement from an output of the scatterometer.

The interferometer and scatterometer are integrated on the same optical head. The first and second spot may be concentric or may be separated in position along said surface under measurement. The signal processor compensates for any time/distance delay due to the displacement between the first and second spot so that the resulting analysis is aligned as between scatterometric and interferometric measurements.

The interferometer may be a resonator-enhanced interferometer such as a Fabry-Perot interferometer, that may include a lens internal to the resonator. The first spot may be introduced within the resonant field by a reflector or by an aperture in a partially reflective surface forming part of the resonator.

The foregoing and other objects, features, and advantages of the invention will be apparent from the following, more particular, description of the preferred embodiment of the invention, as illustrated in the accompanying drawings.

BRIEF DESCRIPTION OF THE DRAWINGS

FIG. 11 is an illustration of an optical measurement system in accordance with another embodiment of the present invention, in which a hole detector provides for co-linear scattering and interferometric illumination.

FIG. 12 is an illustration of an optical measurement system in accordance with another embodiment of the present invention, in which the scattering and interferometric illumination are provided co-linearly.

DESCRIPTION OF ILLUSTRATIVE EMBODIMENT

The present invention concerns optical measurement systems in which a scatterometer and interferometer are included on the same optical head, in order to provide improved detection and measurement capability. The scatterometer provides for sensitive and rapid detection of surface artifacts, while the interferometer provides measurement of the shape and size of the artifacts, in particular, their height and/or volume. Interferometric measurement can be triggered in response to detection of an artifact via the scatterometer, so that rapid scanning of the surface for artifact detection can be performed until an artifact is detected, at which time the artifact's size can be determined via the interferometer. Alternatively, the interferometric measurement can be triggered by either scattering into the interferometer or by amplitude and/or phase thresholds applied to the interferometric channel so that surface artifacts having very low scattering levels will also be detected and measured. The interferometric channel may provide both height information (given by the interferometric phase) as well as amplitude information (i.e., the intensity of the returning signal). The amplitude information is used to determine local surface reflectivity and/or artifact presence. The illumination spots of the interferometer and scatterometer may be concentric, may partially overlap, or may be displaced from each other by a fixed and well-correlated displacement. Although the primary use of the scattering channel is for artifact detection, the scattering channel can also be used for artifact characterization, in particular, for distinguishing between scattering and non-scattering artifacts of non-zero height.

Figure 1:
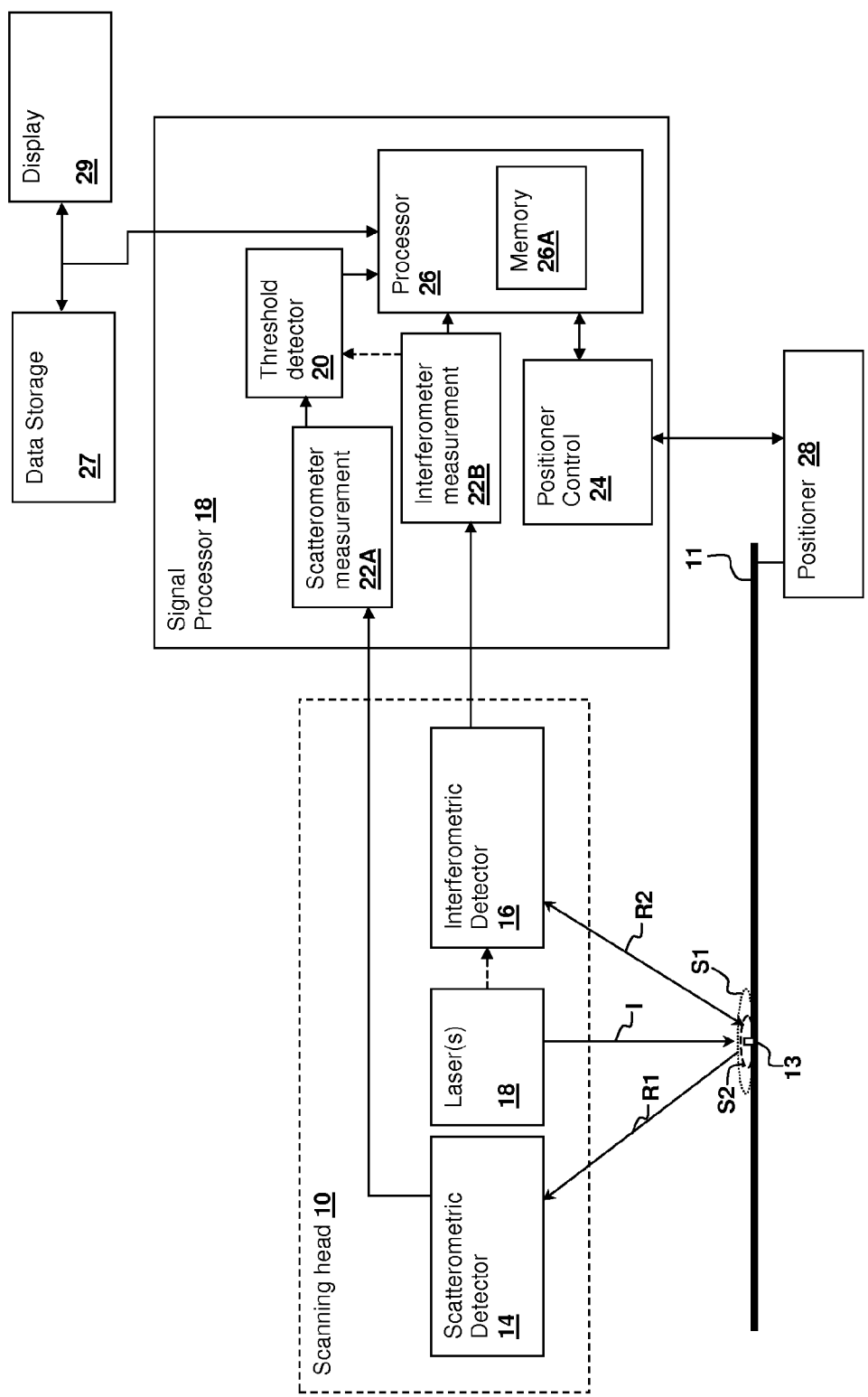
FIG. 1 is a block diagram depicting an optical measurement system in accordance with an embodiment of the present invention.

Referring now to FIG. 1, an optical measurement system in accordance with an embodiment of the present invention is shown. A scanning head 10 is positioned over a surface under measurement 11, which is moved via a positioner 28 that is coupled to a signal processor 18. From scanning head 10, illumination I of surface under measurement 11 is provided by a laser source 18, which may include multiple lasers having separate interferometric and scatterometric wavelengths, as will be illustrated in further detail below. An interferometric detector 16 receives light from an interferometric optical path R2 and a scattering detector 14 receives light from a scatterometric optical path R1. Interferometric optical path R2 returns light from a spot S1, which may be a phase-specific reflection for interference with light coupled from laser 18 via a Michelson fringe-counting interferometer or Doppler interferometer, or may be the return signal from a resonator, such as a Fabry-Perot cavity formed over surface under measurement 11. Scatterometric optical path R1 returns light gathered from one or more non-specular angles with respect to illumination I and surface under measurement 11, so that light scattered from an artifact 13 (which may be a surface defect or feature, or an extraneous particle) disposed on surface under measurement 11, indicates the presence of the artifact. Scatterometric optical path R1 may include multiple optical paths at differing angles, so that differences in scattering angle can be detected by multiple detectors within scattering detector 14. Scatterometric optical path R1 may also include non-specular light returned from the interferometric illumination.

While the illustration shows a positioner 28 for moving surface under measurement under scanning head 10, it is understood that scanning head 10 can be moved over a fixed surface, or that multiple positioners may be employed, so that both scanning head 10 and surface under measurement 11 may be moved in the measurement process. Further, while scattering detector 14, interferometric detector 16 and laser 18 are shown as included within scanning head 10, optical fibers and other optical pathways may be provided for locating one or more of detectors 14, 16 and/or laser(s) 18 physically apart from scanning head 10.

Signal processor 18 includes a processor 26 that includes a memory 26A for storing program instructions and data. The program instructions include program instructions for controlling positioner 28 via a positioner control circuit 24, and performing measurements in accordance with the outputs of interferometric detector 16 and scatterometric detector 14 via an interferometer measurement circuit 22B and a scatterometer measurement circuit 22A that include signal processing and analog-to-digital conversion elements as needed for receiving the outputs of interferometric detector 16 and scatterometric detector 14. A dedicated threshold detector 20 can be employed to indicate to processor 26 when scattering from an artifact 13 on surface under measurement 11 has been detected above a threshold, or when the height or amplitude measured by the interferometric channel have crossed a detection threshold. Signal filtering can be employed in either or both channels as is commonly employed in optical measurement systems. Processor 26 is also coupled to an external storage 27 for storing measurement data and a display device 29 for displaying measurement results, by a bus or network connection. External storage 27 and display device 29 may be included in an external workstation computer or network connected to the optical measurement system of the present invention by a wired or wireless connection. The high-resolution interferometric measurements that are triggered by the scattering or interferometric channel may be processed in real-time by the processor. If the data are processed in real-time, reduced data including specific defect measurement, characterization and location may be transmitted to the workstation system, which reduces the need for local data storage. The data may be processed in electronics included in the optical head and reduced data transmitted to an external system, or the data may be reduced by a dedicated processing unit external to the optical head and then transmitted to a workstation computer system. Alternatively, all of the raw data gathered by the interferometric and scattering channels may be transmitted, to the external workstation for further processing, which may be commenced upon triggering of the high-resolution measurement.

Figure 2B:
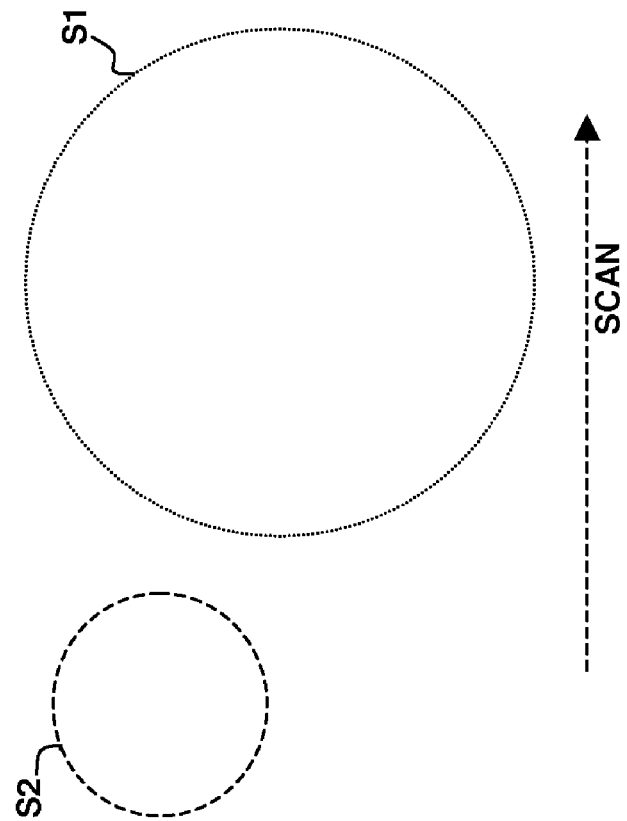
FIGS. 2A and 2B are pictorial diagrams depicting a relationship of scatterometer and interferometer beams in an optical system in accordance with embodiments of the present invention.
Figure 2A:
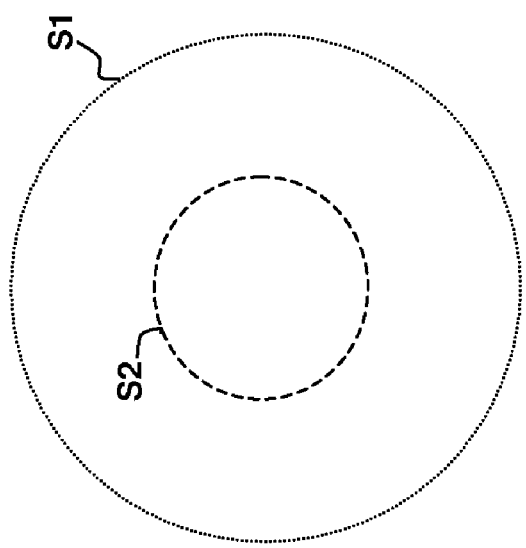

Referring now to FIG. 2A, an arrangement of illumination and measurement spots on a surface of interest as provided by a scatterometer-interferometer in accordance with an embodiment of the present invention is shown. In the depicted embodiment, scatterometer spot S2 is included within interferometer spot S1 and the spots are concentric. Such an arrangement can be adjusted optically to ensure that the spots are concentric, and is particularly useful for systems in which the interferometric and scatterometric measurements are performed continuously and simultaneously.

Referring now to FIG. 2B, an arrangement of illumination and measurement "spots" for a scatterometer-interferometer in accordance with another embodiment of the present invention is shown. In the depicted embodiment, scatterometer spot S2 precedes interferometer spot S1 in the scanning direction, so that interferometric measurement may be triggered in response to detecting an artifact within scatterometer spot S2. Since the displacement between interferometer spot S1 and scatterometer spot S2 is fixed and can be precision-calibrated, the trigger time for interferometric measurement can be determined by knowing the velocity of positioner 28. In general, interferometric measurement will be pre-triggered so as to gather data before the artifact enters interferometer spot S1 and continue to gather data until the artifact has left interferometer spot S2, so that a complete signature of the artifact and its surrounding area is obtained. Pre-detection is an inherent consequence if the scattering spot precedes the interferometric spot in the scanning direction. However, it is possible to have interferometer spot S1 precede the scatterometer spot S2. Pre-triggering by the scattering channel is then achieved by inserting an appropriate electronic (or algorithmic) delay in the data path in the interferometric channel. A delay may also be employed even when the scattering spot precedes the interferometric spot in order to ensure collection of a sufficient amount of data regarding the area of the surface of interest surrounding an artifact. It is also understood that an analogous procedure will be followed when the two spots are separated geometrically and their centers do not lie in-line along the scanning path. A multi-track delay algorithm is more complicated than a single-track delay algorithm, but can be implemented in a straightforward manner in a processing system. Further, the system may operate in a manner such that the surface is first scanned substantially as described above and the location of each triggered artifact is stored. Subsequently, each defect location is re-scanned at higher resolution, generally using a slower scanning speed, in order to obtain a better artifact characterization. Additionally, the system may select particular types of artifacts, while ignoring others during re-scanning, by applying certain criteria. For example, the system may re-measure particular defects that have produced a height or depth signal exceeding a given threshold in an earlier scan, or the system may re-measure only the defects having "height up" values, which are commonly more detrimental in applications such as storage media inspection.

Figure 3:
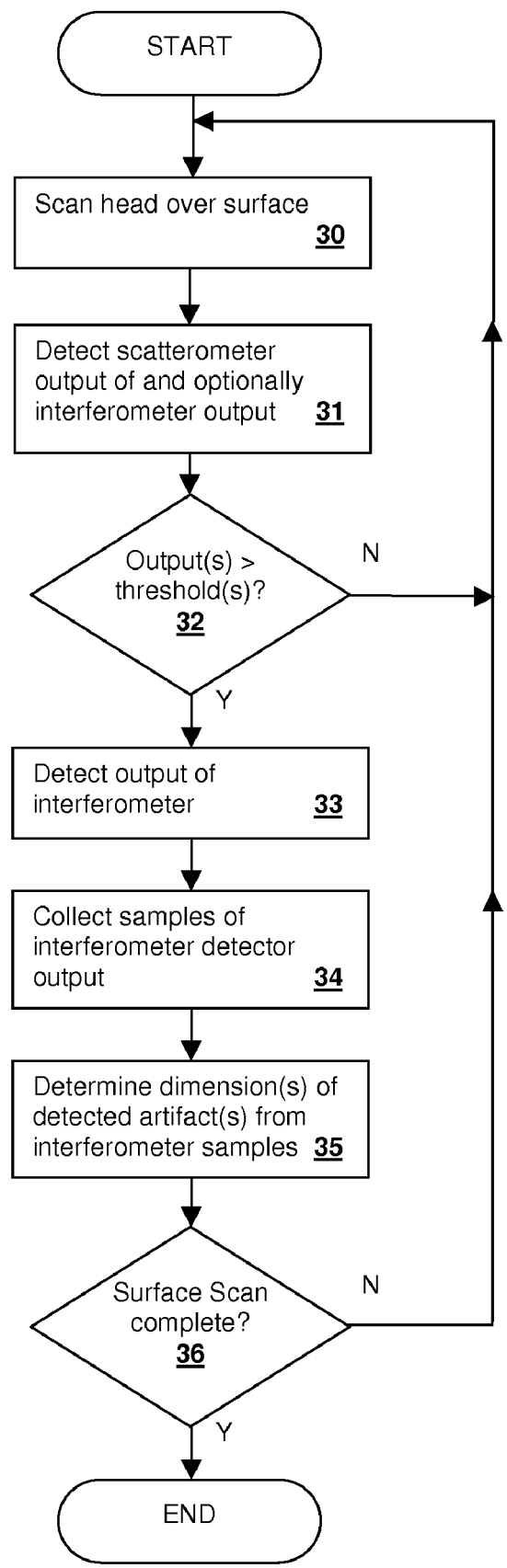
FIG. 3 is a flowchart depicting a method in accordance with an embodiment of the present invention.

Referring now to FIG. 3, a method in accordance with an embodiment of the present invention is illustrated. The method is a method of operation of an optical measurement system in accordance with an embodiment of the present invention as may be implemented by a computer-program product embodied by program instructions stored within memory 26A of FIG. 1. Surface under measurement 11 is scanned by scanning head 10 (step 30) and the output of the scatterometer (and optionally the interferometer) is detected (step 31). If the output of the scatterometer (and optionally the interferometer) exceeds a threshold (decision 32), then the output of the interferometer is detected (step 33) and samples of the interferometer detector output are collected (step 34). The dimension(s) of the detected artifact is determined from the interferometric samples (step 35). Until the surface scan is complete (decision 36), method steps 30-35 are repeated. Variations on the above method are contemplated and the above method is provided only as an example of one technique that may be employed in operating a system in accordance with an embodiment of the present invention. For example, analysis step 35, may be performed only after the surface scan is complete on data collected during the entire scan. As another example, interferometric and scatterometric measurement may be performed continuously, with step 32 either omitted, or performed as part of the post-scanning measurement data analysis. Further, the method mentioned above may be employed, in which locations of artifacts having scattering (and optionally interferometric) measurement values exceeding a threshold are stored, and then a higher-resolution scan is performed using the interferometric channel to measure the artifact sizes.

Figure 4A:
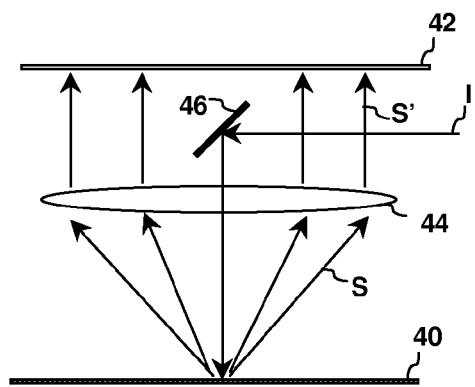
FIGS. 4A-4D are illustrations depicting scatterometer configurations as may be employed in the system of FIG. 1.
Figure 4B:
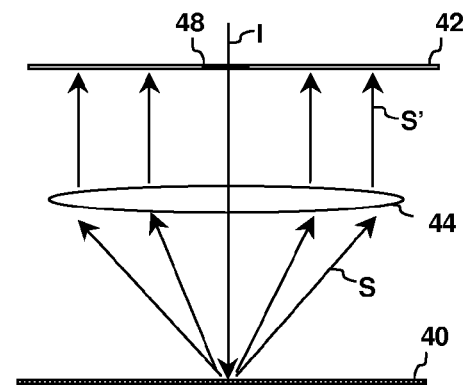

Referring now to FIGS. 4A-4D, scatterometer configurations that may be employed within scanning head 10 of FIG. 1 are illustrated. Like reference numerals in FIGS. 4A-4D indicate like elements and therefore will not be described repeatedly with respect to each Figure. FIG. 4A illustrates a scatterometer configuration in which a small bending mirror 46 is used in the illumination I path to provide illumination normal to a surface under measurement 40. A detector 42, which may be a line detector or an area detector, detects light that is scattered from artifacts disposed on surface under measurement 40 that lie in the focus of a lens 44. Lens 44 collects the scattered light from paths S and directs it to detector 42 along paths S'. The size of bending mirror 46 is chosen to block light specularly reflected from surface under measurement 40. Other techniques such as placing masks or using obstructive apertures in the optical path from surface under measurement to scattering detector(s) 42 can be used to ensure that the dark field of the scatterometer does not include specularly reflected light. FIG. 4B illustrates an alternative scatterometer configuration employing a central aperture 48 in detector 42, through which illumination I is directed to surface under measurement 40 through lens 44 and back through lens 44 and aperture 48, so that any specularly reflected light travels through detector 42, rather than illuminating the active surface of detector 42.

Figure 4C:
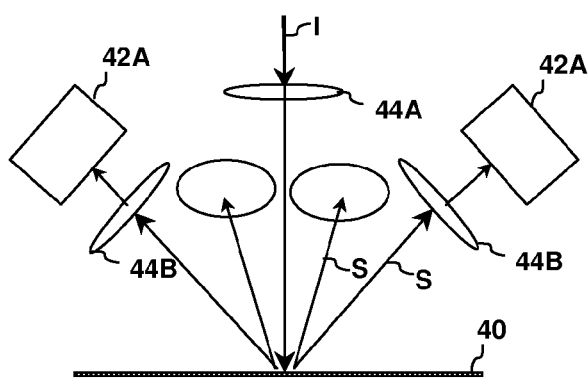
Figure 4D:
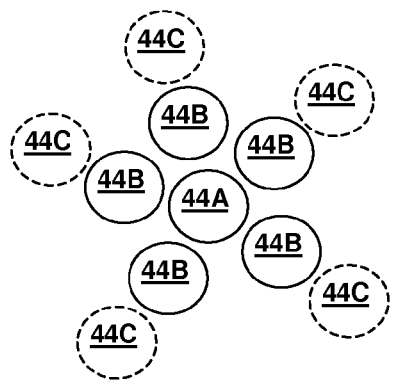

FIG. 4C illustrates yet another alternative scatterometer configuration in which collecting lenses 44B are disposed at one or more predetermined angles with respect to the nominal plane of surface under measurement 40, so that scattering detectors 42A receive light scattered at those angles from artifacts disposed on surface under measurement 40. Illumination is provided through lens 44A and specularly reflected light is avoided in the field of detectors 42A by the orientation of lenses 44B away from the direction normal to surface under measurement 40. FIG. 4D illustrates a top view of the configuration of FIG. 4C, showing a possible orientation of five lenses 44B around lens 44A with an optional second ring of lenses 44C providing scattering detection at another angle further away from the normal to surface under measurement 40. Lenses 44A-44C may be mounted or fabricated on a dome-shaped surface. Various other combinations of quantity, positions, shapes and sizes of lenses for scattering detection may be employed with a goal of collecting as much of scattered light as possible. It is understood that each of the lenses may be equipped with its own scattering detector, or that groups of lenses may be associated with a per-group detector. The coupling of the collected light to the detector can be by free-space propagation as illustrated in FIG. 4B, or by using the lenses as collimators and coupling the collimated light into fibers conducting the collected light to the detectors, or by other suitable collection techniques.

In each of the above-illustrated configurations, illumination is provided normal to surface under measurement 40. However, illumination can be provided at other angles of incidence and it may be desirable to do so, for example, when surface under measurement 40 is a grating or has features patterned that yield a scattering peak in a direction other than normal, so that scattering by those features is suppressed in favor of detection of unexpected artifacts or defects.

Figure 5A:
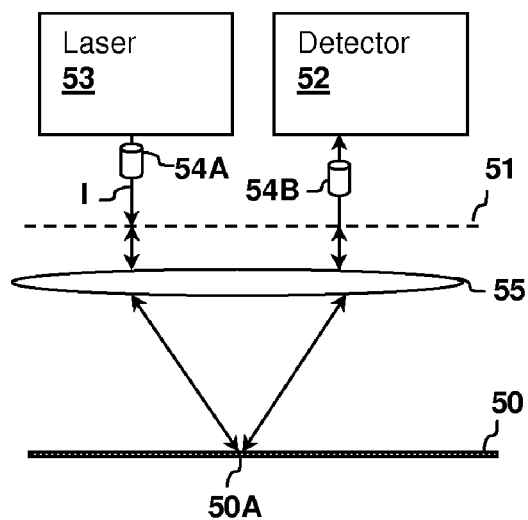
FIGS. 5A and 5B are illustrations depicting interferometer configurations that may be employed in the system of FIG. 1.
Figure 5B:
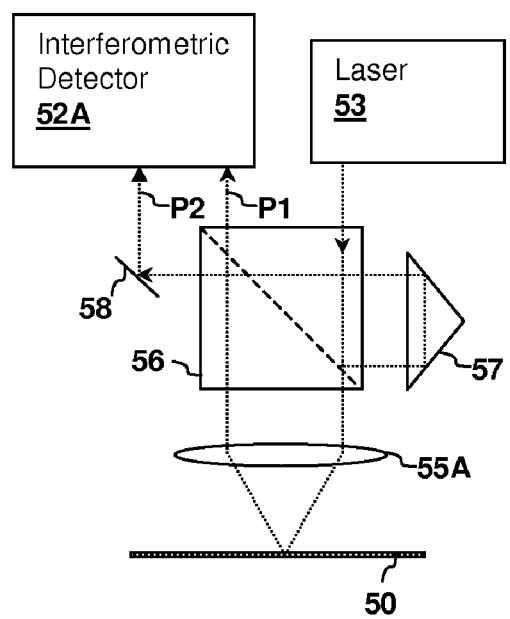

Referring now to FIGS. 5A-5B, interferometer configurations as may be employed in scanning head 10 of FIG. 1 are illustrated. FIG. 5A illustrates a Fabry-Perot interferometer including a lens 55, such as those disclosed in the above-incorporated U.S. Pat. No. 7,022,978. A surface under measurement 50 has a very small measurement spot 50A coupled to two regions on a partially-reflective surface 51 by lens 55. Laser 53 provides illumination of surface under measurement 50 through a collimator 54A, partially reflective surface 51 and lens 55. The illumination spot on partially reflective surface 51, which is the first region, is resonantly coupled to a corresponding second region on partially reflective surface 51 from which light is coupled by a receiving collimator 54B and provided to a detector 52. The intensity of light received at detector 52 is a function of the resonant path length between the above-described regions on partially reflective surface 51, which is affected by the height and size of any artifacts on surface under measurement 50. The height of partially reflective surface 51 can be made electrically adjustable as described in the above-incorporated U.S. Patents so that various attributes of artifacts on surface under measurement 50 can be measured. Also, fringe-counting electronics or Doppler electronics may be included in the system of the present invention and used to perform height measurements.

In FIG. 5B, another interferometer configuration that may be employed within scanning head 10 of FIG. 1 is shown. The depicted interferometer implements a Michelson interferometer that includes an interferometric detector 52A that yields a detected intensity corresponding to the phase difference between light travelling on a measurement path P1 and a reference path P2. A beam splitter 56 splits the illumination provided from laser 53, which is directed through lens 55A to surface under measurement 50 and also to corner retro-reflector prism 57. Light propagating along reference path P2 leaves prism 57 and is directed to interferometric detector 52A by a mirror 58. Light propagating along measurement path P1 is reflected by surface under measurement 50 collected by lens 50A and passes through beamsplitter 56 to detector 52A, where it is interfered with the light collected from reference path P2 to yield an intensity proportional to the phase difference, which is detected to provide a phase output that deviates with the dimension of an artifact disposed on surface under measurement 50. Instead of fringe counting, a Doppler principle can be alternatively employed by measuring the frequency shift of the light along the path P1 relative to reference path P2.

The separate scatterometers shown in FIGS. 4A-4D and interferometers shown in FIGS. 5A-5B provide subsystems that may be included within scanning head 10 of FIG. 1, and in particular, can be used to provide the leading-trailing spot configuration illustrated in FIG. 2B. Additional embodiments of the present invention provide various overlapping and/or concentric spot implementations that result in very compact arrangements suitable for use in high-speed optical inspection systems.

Figure 6A:
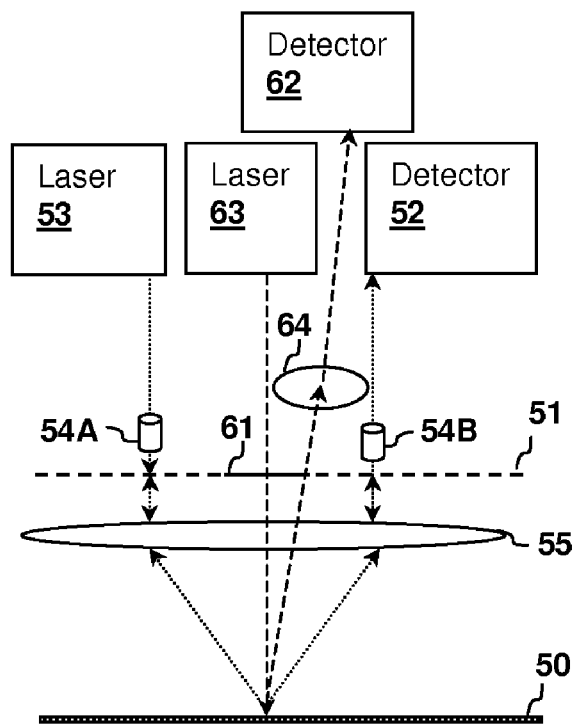
FIGS. 6A and 6B are a side-view and top view illustration, respectively, of an optical measurement system in accordance with an embodiment of the present invention.
Figure 6B:
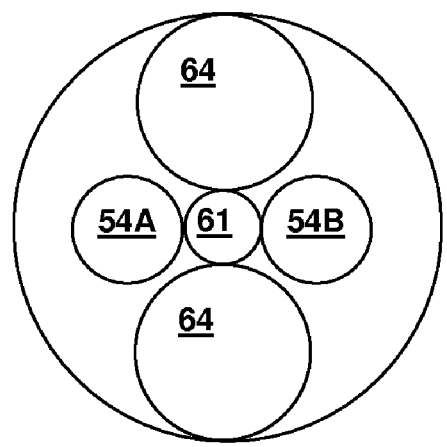

Referring now to FIGS. 6A and 6B, an optical measurement system in accordance with an embodiment of the invention is depicted. The depicted system has an integrated scatterometer-interferometer, in which dashed lines are used to show the scatterometer optical paths and dotted lines are used to show the interferometer optical paths, a schema that is used consistently throughout the remainder of the Figures. A laser 53 provides illumination of surface under measurement 50 for the interferometer through a collimator 54A. Detection of the interferometer signal is provided by a detector 52, which receives the output of a Fabry-Perot interferometer configuration, as illustrated in FIG. 5A and described above, including a lens 55 and a partially reflective surface 51. In FIGS. 6A and 6B a Fabry-Perot interferometer is illustrated. However, a Michelson interferometer may be alternatively employed in the configuration of FIGS. 6A and 6B, as well as the configurations that follow.

Illumination of surface under measurement 50 for the scatterometer is provided from a second laser 63, which may have a wavelength differing from that of laser 53. The wavelength of laser 63 is generally chosen to be as short as possible, as scattering detection improves as the illumination wavelength becomes shorter. One or more lenses 64 are positioned in a configuration similar to that illustrated in FIGS. 4C and 4D as described above and may be located substantially along an axis perpendicular to the axis along which the interferometer's beams extend, as illustrated in FIG. 6B, which shows collimators 54A and 54B displaced along a first axis and lenses 64 displaced along the other. Partially reflective surface 51 is either completely dichroic, so that the scattered light collected by lens(es) 64 is unaffected by passage through partially reflective surface 51, or alternatively, lens(es) 64 are positioned such that the scattered light collected by lens(es) 64 does not pass through partially reflective surface 51. For this purpose, partially reflective surface 51 may be truncated in the direction of lenses 64. Lenses 64 and collimators 54A and 54B are shown as circular in profile, but in practice can be any shape required to maximize the collection of scattered light, while still providing suitable operation of the interferometer. The collected and collimated scattered light provided from collimator 54B is detected by a scatterometer detector 62. If desired, interferometric detector 52 and scattering detector 62 can be equipped with appropriate wavelength-selective filters.

Unless partially reflective surface is dichroic in its entirety as described above, a hole or transparent/dichroic aperture 61 in partially reflective surface 51 provides for introduction of illumination from laser 63 through partially reflective surface 51. Any dichroic characteristic of partially-reflective surface 51, which may be provided by an appropriate coating, should be highly transparent at the wavelength of the scatterometer illumination provided from laser 63, while maintaining the desired reflectivity at the wavelength of the interferometer illumination provided from laser 53.

Figure 7A:
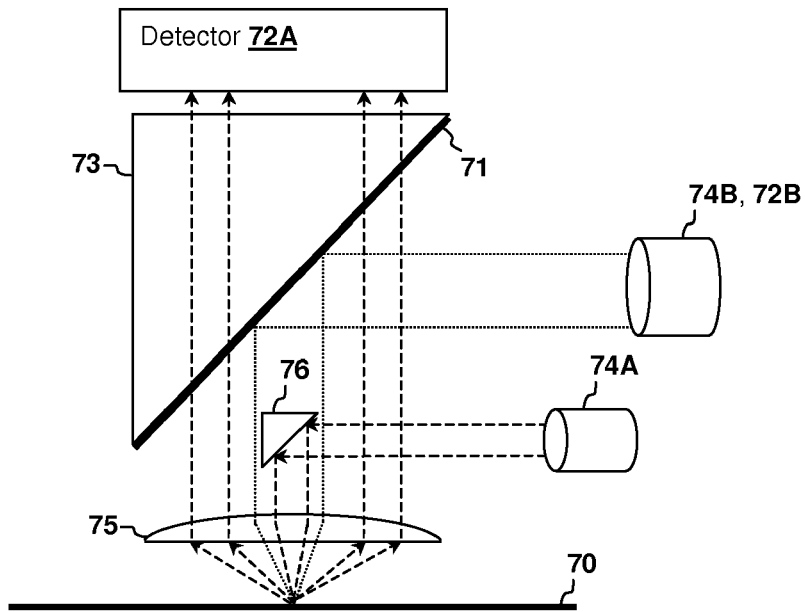
FIGS. 7A and 7B are a side-view and top view illustration, respectively, of an optical measurement system in accordance with another embodiment of the present invention.
Figure 7B:
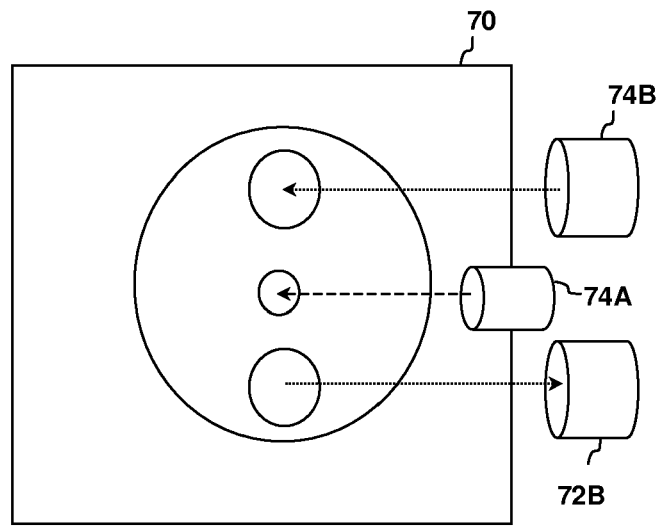

Referring now to FIGS. 7A-7B, an optical measurement system in accordance with another embodiment of the present invention is illustrated. In the illustrated embodiment, a dichroic coating 71 on a primary bending mirror 73, provides for bending of the interferometric beams provided from a laser 74B and received by a detector 72B, which may be arranged in a Michelson or Fabry-Perot configuration. The partially-reflective surface in a Fabry-Perot configuration may be located within detector 72B, or alternatively along the path of the interferometric beam returning from surface under measurement 70 to detector 72B. Scatterometer illumination is provided by an illumination source 74A (laser/collimator) and is directed toward surface under measurement 70 by a small second bending mirror 76, which is sized so as to minimize the disruption of the interferometer. A lens 75 focuses the scattering illumination provided from second bending mirror 76 and the interferometer beams at a point on surface under measurement 70 and collects light scattered from artifacts on surface under measurement 70. The collected scattered light passes through dichroic coating 71 to a large area detector 72A, such as a PIN or avalanche photodiode or photomultiplier that provides the scatterometer output. The depicted embodiment has advantages in that the collection of scattered light is more complete than in the other embodiments described above, and has a relatively simple configuration, using a single lens for the scatterometer and interferometer spot formation and return light collection.

FIG. 7B depicts a top view of the above-described system, showing the arrangement of interferometer laser 74B and detector 72A, as well as the position of scatterometer laser 74A. The symmetric displacement of interferometer laser 74B and detector 72B provides the V-shaped configuration of the interferometric channel as exemplified in FIGS. 5A and 5B, but extending in a direction perpendicular to the plane of the view of FIG. 7A.

Figure 8A:
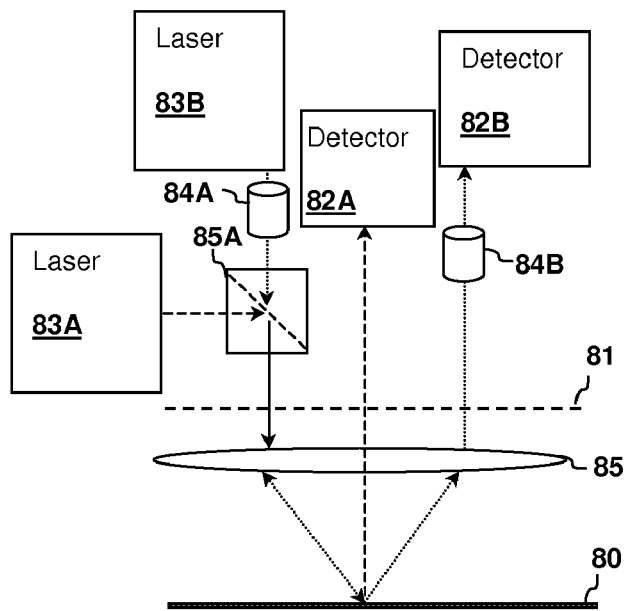
FIGS. 8A and 8B are a side-view and top view illustration, respectively, of an optical measurement system in accordance with another embodiment of the present invention, in which scatterometric and interferometric illumination is made from a co-linear beam.
Figure 8B:
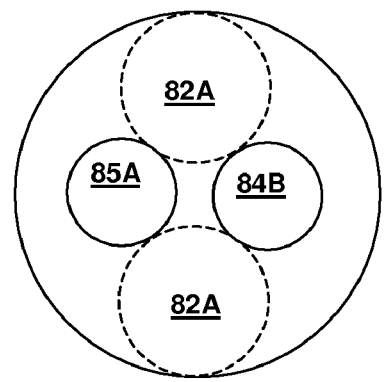

Referring now to FIGS. 8A and 8B, an optical measurement system in accordance with another embodiment of the present invention is shown, in which scatterometric and interferometric illumination is provided in a co-linear beam. In the depicted embodiment, a beam combiner 85A is used to combine the outputs of scatterometer laser 83A and interferometer laser 83B/collimator 84A. A partially reflective surface 81 provides for a Fabry-Perot resonator between areas on partially reflective surface 81 and the resonant path includes the illumination spot on surface under measurement 80. Collimator 84B and detector 82B provide a detection system for the Fabry-Perot interferometer. Scattered light is detected by detector 82A, which may have collecting lenses or other optical components arranged in the direction perpendicular to the plane of FIG. 8A as multiple detectors/collectors 82A as shown in FIG. 8B. As in the other embodiments described above, and other embodiment of the invention described below, the wavelength of scatterometer laser 83A is generally chosen as shorter than that of interferometer laser 83A and should be of sufficiently high power to ensure detection of the artifacts desired for detection. Further, in the present embodiments and the various embodiments that follow, any partially reflective surfaces employed to implement a Fabry-Perot resonator that also lie within the illumination and/or detection path(s) of the scatterometer, should be di-chroic so as to be transparent at the wavelength of the scatterometer illumination laser.

Figure 9A:
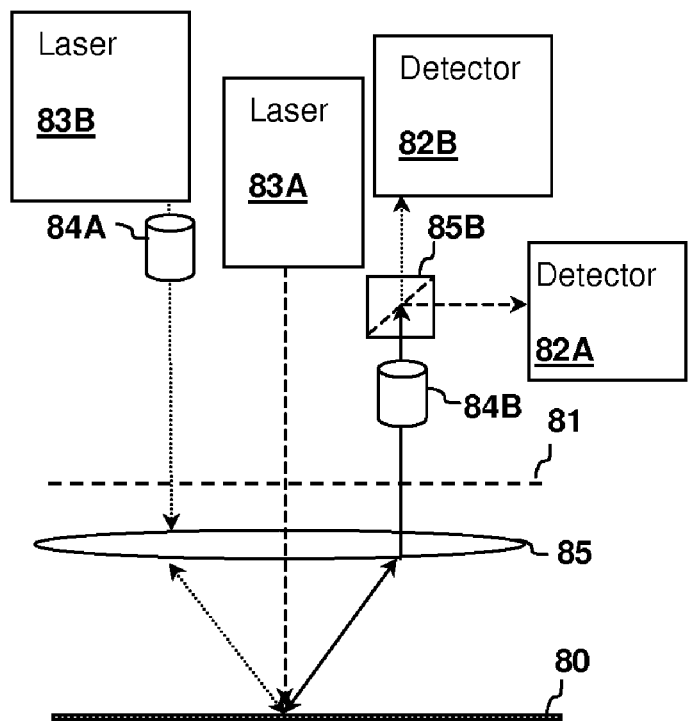
FIGS. 9A and 9B are a side-view and top view illustration, respectively, of an optical measurement system in accordance with another embodiment of the present invention, in which scatterometric and interferometric detection is made from a co-linear beam.
Figure 9B:
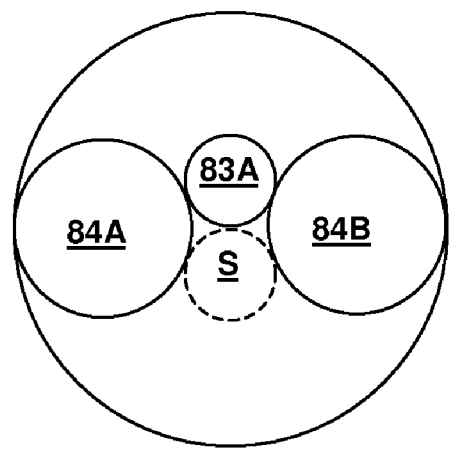

Referring now to FIGS. 9A and 9B, an optical measurement system is shown, in which scatterometric and interferometric detection is made from collinear beams or near collinear beams, in accordance with an embodiment of the present invention. In the depicted embodiment, scatterometric illumination is provided from a first laser 83A and interferometric illumination is provided from a second laser 83B and associated collimator 84A. A partially reflective surface 81 provides for a Fabry-Perot resonator between areas on partially reflective surface 81 and the resonant path includes the illumination spot on surface under measurement 80. A di-chroic beam-splitter 85B separates the beams received and collimated by collimator 84B into a scattering component detected by detector 82A and an interferometric component detected by detector 82B. FIG. 9B shows a top view of the arrangement of collimators 84A and 84B, along with illumination laser 83A. Specular spot S is the specularly reflected illumination, which is avoided in the measurement detection by the placement of collimator 84B. The depicted embodiment provides for particularly compact designs, since the Fabry-Perot interferometer and scatterometer light collection are combined in one collimator 84B. As an alternative to di-chroic beamsplitter 85B, an ordinary beamsplitter can be used instead, and wavelength-selective filters can be included at detectors 82A and 82B so that each detector receives only light of the appropriate wavelength. Alternatively, the illumination wavelengths can be sufficiently separated so that detectors 82A and 82B can be employed having inherent sensitivity to different wavelengths such that isolation between the scattering and interferometric beams is achieved without the use of wavelength-selective filters, or a combination of the two approaches may be employed.

Figure 10A:
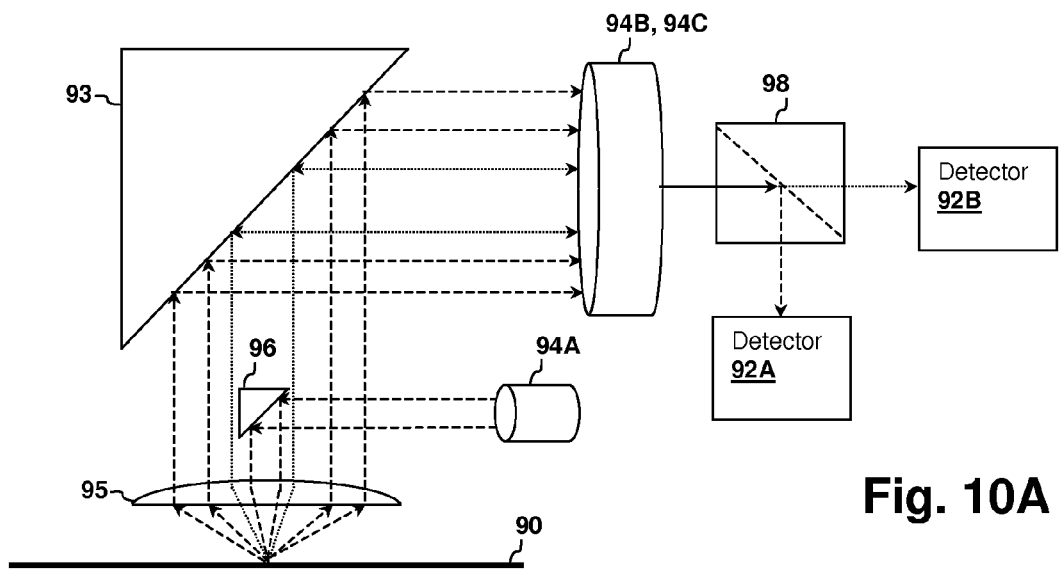
FIGS. 10A and 10B are a side-view and top view illustration, respectively, of an optical measurement system in accordance with another embodiment of the present invention, in which scatterometric and interferometric detection is made from a co-linear beam.
Figure 10B:
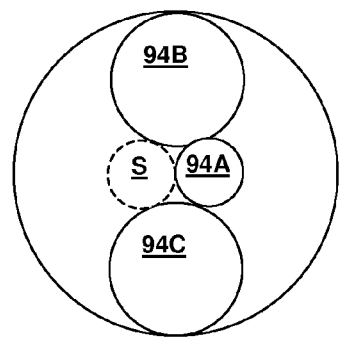

Referring now to FIGS. 10A and 10B, an optical measurement system is shown, in which scatterometric and interferometric detection is made from a co-linear beam, in accordance with another embodiment of the present invention. In the depicted embodiment, a large mirror implemented as a reflecting prism 93 is used to direct both the scatterometric and interferometric measurement beams, returned from surface under measurement 90 through collecting lens 95, to a large collimator 94B and a di-chroic beam-splitter 98 is again used to split the scatterometric beam to a detector 92A and the interferometric beam to a detector 92B. As mentioned above with respect to FIGS. 9A and 9B, an ordinary beamsplitter can be used instead of di-chroic beamsplitter 98 and detectors 92A and 92B can be equipped with wavelength selective filters. Interferometric illumination is provided by a collimator 94C, which is located alongside collimator 94B in the direction of the Figure. The partially-reflective surface in a Fabry-Perot configuration may be located at collimator 94C, or alternatively along the path of the interferometric beam returning from reflecting prism 93 to detector 92B. Collimators 94B and 96C are arranged on opposite sides of the centerline of lens 95 in the direction perpendicular to the Figure.

Scatterometer illumination is provided through a smaller reflecting prism 96, which receives light provided from a laser/collimator 94A. FIG. 10B shows a top view of the arrangement of collimators 94A-94C and specular spot S of the scatterometer illumination is also shown. Additional detection collimators may be provided for greater collection of scattered light and coupled to either the same scattering detector 92A or to additional scattering detectors.

Referring now to FIG. 11, an optical measurement system in accordance with another embodiment of the present invention is shown, in which a hole detector is employed. Laser sources 104A and 104B provide the illumination beams, which are directed through an aperture 108 in a detector 102A. Light scattered from surface under measurement 100 is collected by collecting lens 105 and directed to detector 102A. The return interferometric beam passes through aperture 108 and is split from the specularly scattered light by di-chroic beam-splitter 103 and provided to a detector 102B. As mentioned above, beam-splitter 103 can be replaced with an ordinary beamsplitter and a wavelength selective filter employed at detector 102B.

Referring now to FIG. 12, an optical measurement system in accordance with another embodiment of the present invention is shown, in which the scattering and interferometric illumination are provided co-linearly at a surface under measurement. A first laser 101A provides scatterometric illumination through a di-chroic beam-splitter 113B that reflects the scatterometric illumination to surface under measurement 110, but permits the interferometric beams to pass through. Another di-chroic beam-splitter 113A permits the scattered light gathered from surface under measurement 110 to pass through to wide area detector 112A, but bends the interferometric beam(s) to laser/detector 101B, which can implement a Michelson interferometer. Alternatively, the bottom side of an optical plate 111 that includes beam-splitter 111 can be made partially reflective at the wavelength of laser laser/detector 101B to implement a Fabry-Perot resonator, and laser/detector 101B can include appropriate couplers to provide for isolation of the return light from the illumination. In yet another configuration, a V-shaped orientation as illustrated in FIG. 5A and other embodiments described above may be employed for the interferometer.

Figure 13:
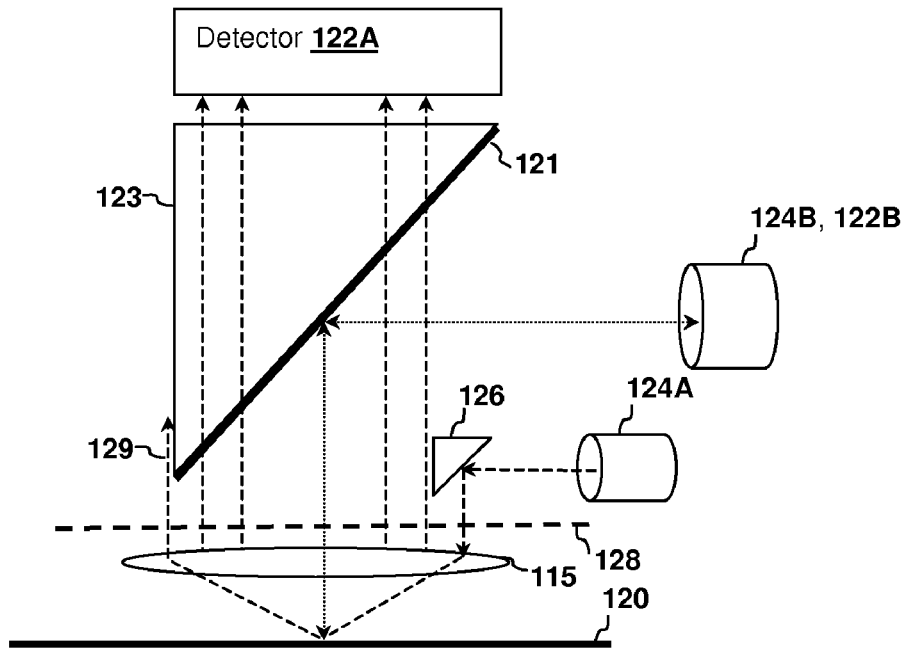
FIG. 13 is an illustration of an optical measurement system in accordance with another embodiment of the present invention, in which scattering illumination is provided away from normal to the surface under measurement.

Referring now to FIG. 13, an optical measurement system in accordance with another embodiment of the present invention is shown, in which scattering illumination is provided away from normal to the surface under measurement. Scattering illumination is provided from a laser/collimator 124A, and bent by a small reflecting prism, so that the scattering illumination impinges on lens 115 away from and parallel with the focal axis of lens 115. The scattering illumination is then focused by lens 115 at a point on surface under measurement 120 at an angle away from normal. The specularly scattered light 129 can then be avoided in the aperture of wide-area detector 122A by the placement of wide-area detector, which detects light scattered at other angles from surface under measurement 120 that passes through a di-chroic surface 121 of beam-splitter 123. The interferometric beams are reflected by di-chroic surface 121 of beam-splitter 123, which are sourced and detected by laser 124A and detector 122B, which as in the interferometer embodiment of FIG. 12, may implement a Michelson interferometer, or a Fabry-Perot interferometer provided by an additional partially reflective surface 128. The interferometric beams may also be configured co-linearly or in a V-shaped configuration as described above with reference to FIG. 12.

Figure 14:
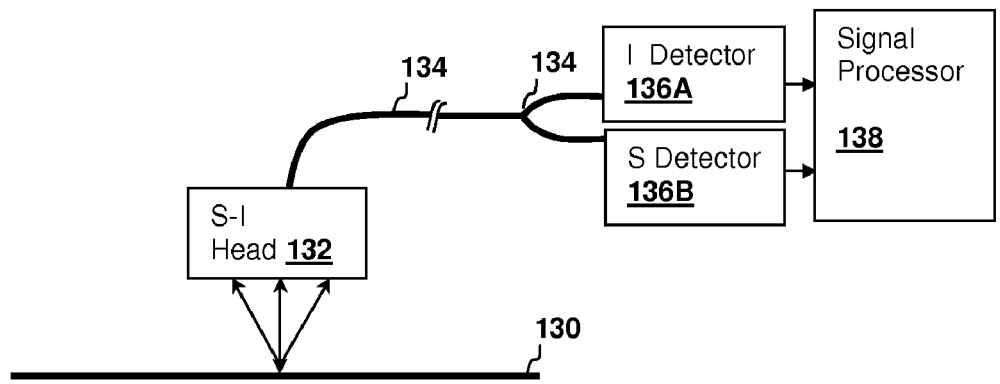
FIG. 14 is an illustration of an optical fiber interconnection scheme in accordance with an embodiment of the present invention.

Referring now to FIG. 14, an optical fiber interconnect scheme is shown in accordance with an embodiment of the present invention. A surface under measurement 130 is scanned by scatterometer-interferometer (SI) head 132 and the return beams are combined in a single optical fiber. Illumination can also be provided by the same fiber using appropriate isolators, but is not a requirement to practice the invention. A fiber beamsplitter 135 splits the output from fiber 134 and provides the split beams to interferometer detector 136A and scatterometer detector 136B, respectively. Output signals from interferometer detector 136A and scatterometer detector 136B are provided to signal processor 138 for further processing as described above. The illustrated configuration provides for a very lightweight optical head with minimum interconnect overhead, as only the collection and illumination apparatus need be mounted on the head, and all of the detection and processing are performed remotely. The only interconnection needed is fiber 134, which can provide a lightweight and flexible interconnect with good durability in flexure. Further, splitter 135 may be a wavelength-selective beamsplitter, providing separate scattering and interferometric beams, or may be a simple fiber splitter that provides identical content (at equal or weighted intensities) and then interferometer detector 136A and scatterometer detector 136B may have differing inherent sensitivities to the scattering and interferometric illumination wavelengths, or wavelength-sensitive filters may be employed as noted above.

While the invention has been particularly shown and described with reference to the preferred embodiments thereof, it will be understood by those skilled in the art that the foregoing and other changes in form and details may be made therein without departing from the spirit and scope of the invention. For example, while each of the above-described embodiments of the invention includes one interferometer channel and one scatterometer channels, multiple interferometers and/or scatterometers may be employed in any combination in order to obtain more information during the same measurement.

What is claimed is:

1. An optical measurement system, comprising:
   a scatterometer integrated within an optical measurement head for detecting light scattered from artifacts on a surface under measurement;
   an interferometer integrated within said optical measurement head and having a single interferometer measurement spot for measuring a magnitude of a deviation of said surface under measurement within said interferometer measurement spot; and
   a signal processor coupled to said scatterometer and said interferometer for detecting presence of said artifacts in response to an output of said scatterometer and determining a dimension of said artifacts in conformity with an output of said interferometer.

2. The optical measurement system of claim 1, wherein said signal processor initiates measurements using said interferometer in response to an output of said scatterometer, wherein a dimension of a given artifact is measured subsequent to detecting said presence of said given artifact using said scatterometer.

3. The optical measurement system of claim 2, wherein said signal processor further initiates measurements using said interferometer further in response to an output of said interferometer, wherein said detecting said presence of said given artifact is determined in conformity with either of an output of said scatterometer and said interferometer.

4. The optical measurement system of claim 1, wherein a scattering measurement spot of said interferometer and said interferometer measurement spot of said interferometer have no overlapping region on said surface under measurement.

5. The optical measurement system of claim 1, wherein a scattering measurement spot of said interferometer and said interferometer measurement spot of said interferometer overlap.

6. The optical measurement system of claim 5, wherein a scattering measurement spot of said interferometer and said interferometer measurement spot of said interferometer are concentric.

7. The optical measurement system of claim 1, further comprising at least one lens positioned between said surface under measurement and both of said scatterometer and said interferometer, whereby light scattered from said surface under measurement and light reflected along an interferometric path of said interferometer are collected for measurement by said scatterometer and said interferometer.

8. The optical measurement system of claim 7, wherein said at least one lens comprise a single lens.

9. The optical measurement system of claim 1, further comprising:
   an interferometer illumination laser for providing illumination of said surface under measurement at a first wavelength for detection by said interferometer; and
   a scatterometer illumination laser for providing illumination at a second wavelength for detection by said scatterometer, wherein said second wavelength differs substantially from said first wavelength.

10. The optical measurement system of claim 9, further comprising a beam combiner for combining an output of said interferometer illumination laser and an output of said scatterometer laser, whereby illumination of said surface under measurement for said scatterometer and said interferometer are provided by a co-linear illumination beam.

11. The optical measurement system of claim 9, further comprising:
   a di-chroic beam splitter for splitting light returning from said surface under measurement into a first beam originating from said interferometer illumination laser and a second beam originating from said scatterometer laser;
   an interferometer detector for receiving said first beam; and
   a scatterometer detector for receiving said second beam.

12. The optical measurement system of claim 1, further comprising:
   a scatterometer detector positioned to receive light scattered from said surface under measurement along a first axis having a first projection along said surface under measurement; and
   an interferometer detector positioned to receive light reflected from said surface under measurement along a second axis having a second projection along said surface of interest, wherein said first and second projection differ in direction.

13. The optical measurement system of claim 12, wherein said first projection is perpendicular to said second projection.

14. The optical measurement system of claim 12, further comprising a partially reflective surface disposed in an optical illumination path between an illumination source of said interferometer and said surface under measurement, and further disposed between said interferometer detector and said surface under measurement along an optical detection path, whereby said interferometer forms a Fabry-Perot interferometer having a V-shaped resonance path partially disposed along said second axis.

15. The optical measurement system of claim 1, wherein said interferometer measures a phase of light returning from said surface under measurement.

16. The optical measurement system of claim 1, further comprising a partially reflective surface disposed in an optical illumination path between an illumination source of said interferometer and said surface under measurement, and further disposed between said interferometer detector and said surface under measurement along an optical detection path, whereby said interferometer forms a Fabry-Perot interferometer.

17. The optical measurement system of claim 1, wherein said scatterometer includes an illumination source for illuminating said surface under measurement from an optical path positioned away from a direction normal to said surface under measurement.

18. The optical measurement system of claim 1, wherein said interferometer measures a frequency shift of light returning from said surface under measurement.

19. The optical measurement system of claim 1, further comprising:
   a scatterometer detector;
   an interferometer detector;
   a beamsplitter having a first output coupled to said scatterometer detector and a second output coupled to said interferometer detector;
   an optical fiber for coupling said interferometer and said scatterometer to said beamsplitter, whereby said beamsplitter, said scatterometer detector and said interferometer detector are located remotely from said optical measurement head.

20. The optical measurement system of claim 19, wherein said scatterometer detector and said interferometer detector have an inherent sensitivity peak at differing wavelengths substantially corresponding to an illumination wavelength of said scatterometer and an illumination wavelength of said interferometer, respectively.

21. The optical measurement system of claim 19, wherein said beamsplitter is an optical fiber beamsplitter.

22. A method of detecting and measuring a size of artifacts disposed on a surface under measurement, said method comprising:
   performing a scatterometric optical measurement to detect the presence of artifacts on a surface under measurement from a scatterometer included in an optical measurement head; and
   performing an interferometric measurement in response to said detected presence of said artifacts, to determine a magnitude of deviation of said surface under measurement due to said detected artifacts using an interferometer included within said optical measurement head.

23. The method of claim 22, wherein said performing an interferometric measurement is commenced in response to said performing a scatterometric measurement detecting said presence of said artifacts.

24. The method of claim 22, wherein said performing a scatterometric measurement further comprises monitoring an interferometric channel of said interferometer and wherein said interferometric measurement is commenced in response to a value of said interferometric channel exceeding a threshold.

25. The method of claim 22, wherein said performing an interferometric measurement comprises illuminating said surface under measurement with a first illumination beam having a first wavelength, wherein said scatterometric measurement comprises illuminating said surface under measurement with a second illumination beam having a second wavelength differing substantially from said first wavelength.

26. The method of claim 25, further comprising combining said first illumination beam and said second illumination beam into a single co-linear beam.

27. The method of claim 25, further comprising:
separating light returning from said surface under measurement into a first component having a wavelength equal to said first wavelength;
separating light returning from said surface under measurement into a second component having a wavelength equal to said first wavelength;
providing said first component to a first detector of said interferometer; and
providing said second component to a second detector of said scatterometer.

28. The method of claim 22, wherein said interferometer is a Fabry-Perot interferometer, and wherein said performing said interferometric measurement determines an intensity of light provided from an output of said Fabry-Perot interferometer.

29. The method of claim 22, wherein said interferometer is a phase-measuring interferometer, and wherein said performing said interferometric measurement determines deviations in a phase of light returned from said surface under measurement.

30. The method of claim 22, wherein said interferometer is a laser Doppler measuring interferometer, and wherein said performing said interferometric measurement measures a frequency shift of light returned from said surface under measurement.

31. The method of claim 22, further comprising:
storing locations of said detected artifacts during said performing a scatterometric optical measurement; and
retrieving said locations of said detected artifacts, and wherein said performing an interferometric measurement to determines said magnitude of deviation of said surface under measurement at said locations during a subsequent scan of said surface of interest after said performing a scatterometric optical measurement is complete.

32. An optical measurement system, comprising an optical head for positioning over a surface under measurement and thereby measuring characteristics of said surface of interest via relative motion provided between said optical head and said surface under measurement, said optical measurement system comprising means for performing a scatterometric measurement for detecting the presence of artifacts on said surface of interest and means for performing an interferometric measurement for determining a size of said detected artifacts.

33. The optical measurement system of claim 32, further comprising triggering means for initiating said interferometric measurement in response to said scatterometric measurement detecting said presence of said artifacts.

34. The optical measurement system of claim 32, wherein said triggering means further comprises means for initiating said interferometric measurement in response to said means for performing an interferometric measurement indicating presence of said artifacts.

35. An optical measurement system, comprising:
an optical measurement head including a scatterometer for detecting light scattered from artifacts on a surface under measurement and an interferometer for measuring a magnitude of a deviation of said surface under measurement;
a detection and signal processing unit for detecting presence of said artifacts in response to an output of said scatterometer and determining a dimension of said artifacts in conformity with an output of said interferometer; and
an optical fiber for coupling an output of said scatterometer and an output of said interferometer to said detection and signal processing unit, whereby said optical fiber provides a single-beam connection between said optical measurement head and said detection and signal processing unit.

36. The optical measurement system of claim 35, wherein said detection and signal processing unit comprises:
a scatterometer detector having an inherent sensitivity peak substantially corresponding to an illumination wavelength of said scatterometer; and
an interferometer detector having an inherent sensitivity peak substantially corresponding to an illumination wavelength of said interferometer.

* * * * *